United States Patent [19]

Liu et al.

[11] Patent Number: 5,217,485

[45] Date of Patent: Jun. 8, 1993

[54] POLYPROPYLENE MONOFILAMENT SUTURE AND PROCESS FOR ITS MANUFACTURE

[75] Inventors: Cheng-Kung Liu, Norwalk; John C. Brewer, Bristol, both of Conn.

[73] Assignee: United States Surgical Corporation, Norwalk, Conn.

[21] Appl. No.: 729,459

[22] Filed: Jul. 12, 1991

[51] Int. Cl.$^5$ .............................................. A61B 17/00
[52] U.S. Cl. ...................................... 606/228; 606/231
[58] Field of Search .......................... 606/231, 228; 264/210.8, 289.6, 290.5, DIG. 73

[56] References Cited

U.S. PATENT DOCUMENTS

| | | | |
|---|---|---|---|
| 3,092,891 | 6/1963 | Baratti . | |
| 3,106,442 | 10/1963 | Compostella et al. | 264/210.8 |
| 3,256,258 | 6/1966 | Herrman | 264/210.8 |
| 3,323,190 | 6/1967 | Boltniew . | |
| 3,330,897 | 7/1967 | Tessier . | |
| 3,359,983 | 12/1967 | Northey | 606/231 |
| 3,413,397 | 11/1968 | Bierbaum et al. | 264/210.8 |
| 3,432,590 | 3/1969 | Papps . | |
| 3,549,743 | 12/1970 | Riordon . | |
| 3,630,205 | 12/1971 | Listner | 606/228 |
| 3,636,956 | 1/1972 | Schneider | 606/230 |
| 4,520,822 | 6/1985 | Menezes et al. | 606/228 |
| 4,577,264 | 12/1985 | Hinsch | 606/228 |
| 4,578,451 | 3/1986 | Weaver et al. | 606/231 |
| 4,620,542 | 11/1986 | Menezes et al. | 606/228 |
| 4,621,638 | 11/1986 | Silvestrini . | |
| 4,671,280 | 6/1987 | Dorbano et al. | 606/220 |
| 4,911,165 | 3/1990 | Lennard et al. | 606/231 |
| 4,970,038 | 11/1990 | Stanko | 264/210.8 |

FOREIGN PATENT DOCUMENTS

0415783A2  3/1991  European Pat. Off. .
1588031    4/1981  United Kingdom .

Primary Examiner—Stephen C. Pellegrino
Assistant Examiner—Gary Jackson
Attorney, Agent, or Firm—Thomas R. Bremer; Peter G. Dilworth; Rocco S. Barrese

[57] ABSTRACT

A process is provided for manufacturing a polypropylene monofilament suture exhibiting reduced strain energy, increased knot security and greater resistance to acquiring an in-storage set.

25 Claims, 1 Drawing Sheet

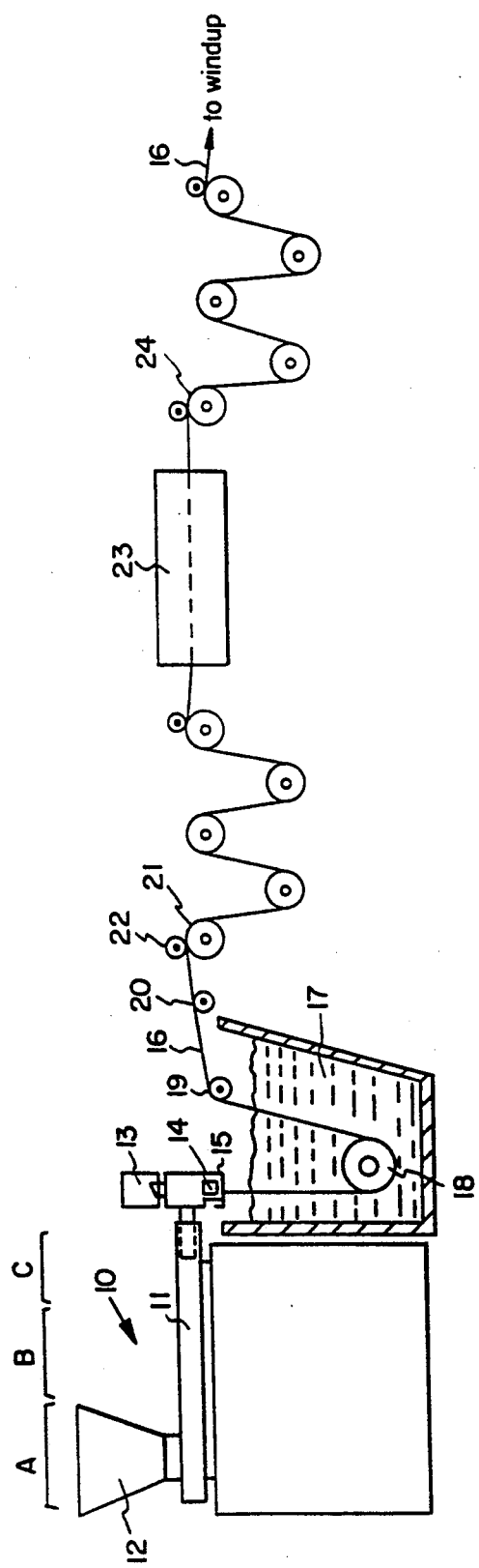

POLYPROPYLENE MONOFILAMENT SUTURE AND PROCESS FOR ITS MANUFACTURE

BACKGROUND OF THE INVENTION

This invention relates to a polypropylene monofilament suture exhibiting improved properties, e.g., reduced strain energy and improved knot security, and to a process for its manufacture.

Sutures fabricated from polypropylene homopolymers and copolymers and from polymer blends containing polypropylene are disclosed in, among others, U.S. Pat. Nos. 3,359,983, 3,630,205, 4,520,822, 4,557,264, 4,620,542, 4,621,638 and 4,911,165 and in U.K. Patent Specification No. 1,588,031 and European Patent Application No. 415,783.

Thus, e.g., in accordance with U.S. Pat. No. 3,630,205, following extrusion an isotactic polypropylene monofilament is quenched to effect its solidification and drawn, or stretched, from six to seven times its original length at elevated temperature resulting in its orientation and an increase in its tensile strength. The stretched monofilament is then collected on a spool for subsequent processing, specifically, an annealing operation which results in the shrinkage of the suture. The various conditions of the extrusion, stretching and annealing steps are indicated to be important for obtaining the desired polypropylene monofilament suture, one which is characterized by an ultimate elongation of from 35 to 63 percent.

The polypropylene monofilament suture manufacturing process of U.S. Pat. No. 4,911,165 is said to provide a suture exhibiting improved compliance while retaining the excellent properties of prior polypropylene monofilament sutures. An increase in the draw ratio during orientation and the allowed shrinkage during annealing is credited with resulting in a monofilament suture of lower modulus at a given level of tensile strength.

SUMMARY OF THE INVENTION

It has been discovered that if in the polypropylene monofilament suture manufacturing process described in U.S. Pat. No. 3,630,205 the stretched monofilament is permitted to equilibrate, or "rest", prior to undergoing the annealing operation, the resulting suture will exhibit significantly improved properties such as reduced strain energy, increased knot security and reduced out-of-package set even after relatively lengthy periods of shelf storage.

In accordance with this invention, in a polypropylene monofilament suture manufacturing process in which an isotactic polypropylene is melt extruded to provide a monofilament and the solidified monofilament is subjected to stretching and annealing to provide the suture, an improvement is provided which comprises equilibrating the stretched monofilament prior to annealing and thereafter annealing the stretched, equilibrated monofilament.

The step of "equilibrating" or "equilibration" in this invention contemplates achieving a stable condition of the polypropylene monofilament such that certain physical properties of the monofilament, e.g., its 0–5% and 0–10% strain energies, as measured upon the annealed suture tend to resist significant change even after extended periods of shelf storage.

While it is disclosed in U.S. Pat. No. 3,630,205 supra, that the stretched polypropylene monofilament after being taken up on a spool can be stored for further processing, nothing is said of the duration of storage. Moreover, there is no recognition or appreciation that a period of storage sufficient to result in equilibration of the monofilament will provide the improved properties observed for the suture of this invention, i.e., reduced energy, increased knot security and the other desirable properties previously mentioned.

As used herein, the expression "strain energy" is the integration of the measured stress-strain curve for a polypropylene monofilament measured in kilograms-mm and is equivalent to the work expended in elongating the monofilament by a specified percentage of its original length. The strain energy of a polypropylene monofilament suture is related to the amount of effort required to straighten the suture upon removal of the suture from its package such that the lower the strain energy, the lesser the effort required to straighten the suture prior to use.

BRIEF DESCRIPTION OF THE DRAWINGS

FIG. 1 is a schematic illustration of apparatus which is suitable for carrying out the extruding and stretching steps of the polypropylene monofilament suture manufacturing process of this invention.

DESCRIPTION OF THE PREFERRED EMBODIMENTS

In general, the conditions of the individual steps of extruding, stretching (orienting) and annealing in the polypropylene monofilament suture manufacturing process of this invention can be substantially the same as those disclosed in U.S. Patent No. 3,630,205, the contents of which are hereby incorporated by reference herein. Similarly, the process herein can employ much the same type apparatus as that described in U.S. Patent No. 3,630,205.

FIG. 1 schematically illustrates the extrusion and stretching operations of the polypropylene monofilament manufacturing operation herein. Extruder unit 10 is of a known or conventional type and is equipped with controls for regulating the temperature of barrel 11 in various zones thereof, e.g., progressively higher temperatures in three consecutive zones A, B and C along the length of the barrel. Pellets or powder of polypropylene resin are introduced to the extruder through drier-hopper 12. Useful isotactic polypropylene resins include those described in U.S. Pat. No. 3,630,205, i.e., those possessing a weight average molecular weight (Mw) of from about 294,000 to about 316,000, a number average molecular weight (Mn) of from about 78,400 to about 82,100 and a calculated dispersity (Mn/Mw) of from about 3.58 to about 4.0. Useful polypropylene resins will advantageously possess a melt flow index in g/10 min of from about 2 to about 6 and preferably from about 3.5 to about 4 5. Isotactic polypropylene resins which can be used herein with generally good results include Resin F040A Blue of Aristech Chemical Corporation (Pittsburgh, Pa.) and Profax 6523 of Himont Incorporated (Wilmington, Del.). These resins possess the following characteristics

|  | Aristech F040A | Profax 6523 |
|---|---|---|
| Weight Average Molecular Weight | 283,000[1] | 305,000[2] |
| Number Average Molecular Weight | 61,000[1] | 80,000[2] |
| Melt Flow Index, g/10 min | 4.5 | 3–5 |

-continued

|  | Aristech F040A | Profax 6523 |
|---|---|---|
| Isotactic Index | 96 | 94 or above |

[1] Measured upon the dyed resin, as reported by the supplier.
[2] In decalin, as reported in the literature.

Motor-driven metering pump 13 delivers extruded resin at a constant rate to spin pack 14 and thereafter through spinneret 15 possessing one or more orifices of desired diameter to provide a molten monofilament 16 which then enters quench bath 17, e.g., containinq water, where the monofilament solidifies. The distance monofilament 16 travels after emerging from spinneret 15 to the point where it enters quench bath 17, i.e., the air gap, can vary and can advantageously be from about 0.5 to about 100 cm and preferably from about 1 to about 20 cm. If desired, a chimney (not shown), or shield, can be provided to isolate monofilament 16 from contact by air currents which might otherwise affect the cooling of the monofilament in some unpredictable manner. In general, barrel zone A of the extruder can be maintained at a temperature of from about 190° to 230° C., zone B at from about 200° to 230° C. and zone C at from about 210° to about 230° C. Additional temperature parameters include: metering pump block 13 at from about 205° to about 230° C., spin pack 14 at from about 205° to about 230° C., spinneret 15 at from about 190° to about 230° C. and quench bath 17 at from about 30° to about 80° C.

Entering quench bath 17, monofilament 16 is passed by driven roller 18 over idler rollers 19 and 20 and thereafter is wrapped around a first godet 21 provided with nip roll 22 to prevent slippage which might otherwise result from the subsequent stretching operation. Monofilament 16 passing from godet 21 is stretched in order to effect its orientation and thereby increase its tensile strength. Thus, in one type of stretching operation, generally suitable for smaller sutures, e.g., sizes 4/0 to 8/0, monofilament 16 is drawn through heating unit 23, which can be an oven chamber or a hot water trough, by means of second godet 24 which rotates at a higher speed than first godet 21 thereby stretching the monofilament from six to seven times it original length. Where heating unit 23 is an oven chamber, its temperature is advantageously maintained at from about 90° to about 180° C. and preferably from about 110° to about 150° C. In the case or larger sutures, e.g., sizes 2 to 3/0, it is preferred that heating unit 23 be a hot water trough or bath which is maintained at a temperature of from about 80° to about 98° C. and preferably from about 86° to about 98° C.

For smaller suture sizes, e.g., sizes 6/0 to 8/0, it is preferred to pass the monofilament through a second heating unit, e.g., maintained at a temperature of from about 80° to about 130° C. and preferably from about 90° to about 110° C., by means of a third godet to heat-treat the monofilament prior to the equilibration and annealing operations. This second heat treatment results in on-line relaxation, or shrinkage, of the monofilament, e.g., for a recovery of from about 97 to about 93 percent, and preferably from about 96 to about 94 percent, of the stretched length of the monofilament. In order to accommodate this on-line shrinkage in the monofilament, the third godet is driven at a speed which is somewhat less than that of the second godet.

Following stretching and orientation (and, optionally, the aforedescribed second heat treating step for smaller suture sizes), polypropylene monofilament 16 from godet 24 is taken up on a spool which is then set aside for a period of time sufficient to permit the monofilament to achieve a condition of equilibration as previously defined. While the period of equilibration may vary depending on the particular polypropylene resin selected and/or the conditions under which the resin is extruded, cooled and oriented, in most cases storage of the monofilament following its orientation for at least about 2 days, preferably at least about 3 days and more preferably at least about 4 days. It is generally preferred that the spooled monofilament be stored at ambient temperature, e.g., 20°-23° C., and a relative humidity of about 50%.

In the larger suture sizes, e.g., sizes 5/0 and larger, annealing is accompanied by shrinkage of the suture, e.g., for a recovery of from about 95 to about 75 percent, and preferably from about 90 to about 85 percent, of its stretched length.

In carrying out the annealing operation, the desired length of equilibrated suture may be wound around a creel and the creel placed in a heating cabinet maintained at the desired temperature, e.g., 150° C., as described in U.S. Pat. No. 3,630,205. After a suitable period of residency in the heating cabinet, e.g., about 10 minutes or so, the suture will have undergone shrinkage, e.g., to about 85% of the stretched length for sutures of sizes 2 to 3/0, to about 90% of the stretched length for sutures of sizes 4/0 and 5/0 and essentially no shrinkage in the case of sutures of sizes 6/0 to 8/0. As shown in U.S. Pat. No. 3,630,205, the creel may be rotated within the heating cabinet in order to insure uniform heating of the monofilament or the cabinet may be of the circulating hot air type in which case uniform heating of the monofilament will be achieved without the need to rotate the creel. Thereafter, the creel with its annealed suture is removed from the heating cabinet and when returned to room temperature, the suture is removed from the creel, conveniently by cutting the wound monofilament at opposite ends of the creel. The annealed sutures, optionally attached to surgical needles, are then ready to be packaged and sterilized.

The sutures of this invention exhibit maximum 0-5% and 0-10% energies which are substantially less that those of other, commercially available sutures. In general, the sutures of this invention will exhibit average maximum energies which are at least about 20%, preferably at least about 30% and more preferably at least about 50% less than the following average 0-5% and 0-10% energies which are characteristic of suture products currently being marketed ("standard polypropylene monofilament sutures"):

| Suture Size | Average 0-5% Strain Energy Kg-mm | Average 0-10% Strain Energy Kg-mm |
|---|---|---|
| 2 | 12.0 | 50 |
| 1 | 10.5 | 42 |
| 0 | 7.5 | 30 |
| 2/0 | 6.0 | 23 |
| 3/0 | 3.5 | 13 |
| 4/0 | 2.5 | 11 |
| 5/0 | 1.5 | 5.5 |

The following examples are illustrative of the polypropylene monofilament suture of this invention and the process for its manufacture.

EXAMPLES 1-10

Table I below sets forth typical conditions for extruding, stretching, optionally heat treating (in the case of suture sizes 6/0 to 8/0), equilibrating and annealing various sizes of polypropylene monofilament suture in accordance with this invention. In descending order, the size of the sutures ranged from 2 to 8/0. All of the sutures were fabricated from Aristech's polypropylene resin F040A Blue whose physical properties are given above.

The average physical properties of the sutures and the procedures employed for their measurement are set forth in Table II as follows:

TABLE II
PROCEDURES FOR MEASURING PHYSICAL PROPERTIES OF POLYPROPYLENE MONOFILAMENT SUTURES

| Physical Property | Test Procedure |
|---|---|
| knot pull tensile strength, kg | U.S.P. XXI, tensile strength, sutures (881) |
| straight pull, kg | ASTM D-2256, Instron Corporation |

TABLE 1
CONDITIONS OF MANUFACTURING VARIOUS SIZES OF POLYPROPYLENE MONOFILAMENT SUTURE

| | Example | | | | | | | | | |
|---|---|---|---|---|---|---|---|---|---|---|
| | 1 | 2 | 3 | 4 | 5 | 6 | 7 | 8 | 9 | 10 |
| | Suture Size | | | | | | | | | |
| Process Conditions | 2 | 1 | 0 | 2/0 | 3/0 | 4/0 | 5/0 | 6/0 | 7/0 | 8/0 |
| Extrusion Operation | | | | | | | | | | |
| extruder screw, rpm | 17.4 | 12.9 | 31.0 | 23.0 | 15.9 | 13.5 | 9.2 | 10.4 | 9.8 | 1.8 |
| barrel temp., °C., zone A | 210 | 200 | 205 | 205 | 200 | 210 | 205 | 215 | 215 | 215 |
| barrel temp., °C., zone B | 220 | 200 | 215 | 215 | 210 | 230 | 225 | 230 | 230 | 230 |
| barrel temp., °C., zone C | 220 | 220 | 215 | 215 | 210 | 230 | 225 | 230 | 230 | 230 |
| barrel pressure, psi | 2290 | 2150 | 2480 | 2180 | 2300 | 2025 | 2100 | 2500 | 2850 | 2800 |
| barrel melt temp., °C. | 229 | 229 | 222 | 220 | 218 | 236 | 230 | 238 | 239 | 235 |
| pump size, cc per revolution | 1.17 | .584 | 1.17 | 1.17 | 1.17 | .297 | .297 | .297 | .297 | .16 |
| pump rpm | 7.9 | 11.4 | 16.2 | 11.8 | 7.35 | 18.1 | 15.6 | 6.1 | 4.68 | 3.7 |
| pump temp., °C. | 205 | 210 | 205 | 205 | 205 | 205 | 205 | 220 | 220 | 220 |
| pump pressure, psi | 1935 | 2210 | 2300 | 1800 | 1900 | 1950 | 2000 | 2700 | 3015 | 2600 |
| pump melt temp., °C. | 215 | 217 | 212 | 211 | 210 | 216 | 213 | 227 | 228 | 225 |
| block temp., °C. | 210 | 210 | 205 | 205 | 205 | 210 | 210 | 220 | 220 | 220 |
| clamp temp., °C. | 215 | 210 | 210 | 205 | 205 | 215 | 210 | 230 | 230 | 230 |
| adapter temp., °C. | 215 | 210 | 210 | 205 | 205 | 215 | 210 | 230 | 230 | 230 |
| filter type | flat | flat | flat | flat | flat | flat | flat | CDL | CDL | CDL |
| filter screen, microns | 20 | 20 | 20 | 20 | 10 | 5 | 5 | 5 | 5 | 1 |
| diameter of spinneret orifices | 2.3 | 2.3 | 1.25 | 1.25 | .75 | .75 | .75 | .50 | .304 | .304 |
| no. of spinneret orifices | 1 | 1 | 4 | 4 | 4 | 4 | 4 | 4 | 4 | 4 |
| spinneret temp, °C. | 200 | 200 | 195 | 195 | 205 | 205 | 200 | 220 | 220 | 220 |
| spinneret pressure, psi | 884 | 740 | 1038 | 940 | 1250 | 800 | 1100 | 880 | 1175 | 1375 |
| spinneret melt temp., °C. | 207 | 203 | 196 | 198 | 198 | 209 | 195 | 211 | 210 | 210 |
| lb/hr output, per orifice | .92 | .66 | .47 | .34 | .21 | .13 | .11 | .04 | .034 | .014 |
| chimney length, cm | 68 | 68 | 23 | 23 | 8 | — | — | — | — | — |
| air gap, cm | 2 | 2 | 12 | 8 | 5 | 1 | 1 | 1 | 1 | 1 |
| quench bath temp., °C. | 80 | 75 | 75 | 75 | 65 | 50 | 40 | 30 | 30 | 30 |
| driven roller, depth | 1 | 1 | 37 | 37 | 5 | 23 | 23 | 10 | 9 | 6 |
| driven roller, rpm | 3 | 3 | 4 | 4 | 5 | 4.5 | 7 | 7 | 7 | 7 |
| Stretching (Orienting) Operation | | | | | | | | | | |
| draw bath temp, °C. | 98 | 98 | 97 | 97 | 86 | — | — | — | — | — |
| first heating chamber temp, °C. | — | — | — | — | — | 130 | 130 | 140 | 140 | 140 |
| first godet, mpm | 5.5 | 5.5 | 6.3 | 6.3 | 7.3 | 7.3 | 10.3 | 9.9 | 10.0 | 10.0 |
| second godet, mpm | 36.2 | 37.5 | 42.0 | 42.0 | 48.7 | 47.4 | 67.3 | 60.3 | 60.0 | 60.0 |
| draw ratio | 6.6 | 6.8 | 6.6 | 6.6 | 6.7 | 6.5 | 6.5 | 6.1 | 6 | 6 |
| Second (Optional) Heat Treating Operation | | | | | | | | | | |
| second heating chamber temp, °C. | — | — | — | — | — | — | — | 90 | 90 | 90 |
| third godet | — | — | — | — | — | — | — | 63.5 | 63.4 | 63.4 |
| shrinkage as % recovery of stretched length | — | — | — | — | — | — | — | 95 | 95 | 95 |
| Equilibration Operation | | | | | | | | | | |
| holding period for equilibration, days | 4 | 4 | 4 | 4 | 4 | 4 | 4 | 4 | 4 | 4 |
| Annealing Operation | | | | | | | | | | |
| annealing temp., °C. | 150 | 150 | 150 | 150 | 150 | 150 | 150 | 150 | 150 | 150 |
| duration of annealing, min. | 10 | 10 | 10 | 10 | 10 | 10 | 10 | 10 | 10 | 10 |
| shrinkage as % recovery of stretched length | 85 | 85 | 85 | 90 | 90 | 90 | 90 | — | — | — |

The physical properties of polypropylene monofilament sutures produced in accordance with the conditions of Table I were measured at 23° F. and 50 percent relative humidity. Measurements of knot pull, percent elongation, tensile strength and strain energy were carried out employing an Instron Corporation (Canton, Mass.) Tensile Tester, model no. 4301, equipped with yarn grips and operated with a gauge length of 127 mm and a crosshead speed of 127 mm/min.

| | |
|---|---|
| elongation at break, % | ASTM D-2256 |
| tensile strength, kg-mm$^2$ | ASTM D-2256, Instron Corporation Series IX Automated Materials Testing System 1.03A |
| 0-5% and 0-10% strain energies, kg-mm | ASTM D-2256, Instron Corporation Series IX Automated Materials Testing System 1.03A |
| knot security | A 2 cm loop is tied with a surgeon's square knot (1 = 1 = 1 = 1) securing the throws at 20% of the USP XXII knot strength (n = 10 loops |

TABLE II-continued
PROCEDURES FOR MEASURING PHYSICAL PROPERTIES OF POLYPROPYLENE MONOFILAMENT SUTURES

| Physical Property | Test Procedure |
|---|---|
| | per group). The loop is placed next to a cloth-wrapped mandrel rotating at .5 rpm. The fixtures are secured to allow contact of the cloth material against the fourth throw or, top throw, of each knot. The cloth wrapping is moistened with 37° C. water prior to the test and is periodically remoistened during the test. After each pass of the cloth across the knot (for a total of 100 passes), the knot is inspected for top throw security. For a knot to be considered secure, the 3 mm ears must not come undone and there must be no relaxation of the knot or loss of the fourth throw. |

Table III below sets forth the average physical properties of the polypropylene monofilament sutures:

TABLE III
PHYSICAL PROPERTIES OF POLYPROPYLENE MONOFILAMENT SUTURES

| | Example | | | | | | | | | |
|---|---|---|---|---|---|---|---|---|---|---|
| | 1 | 2 | 3 | 4 | 5 | 6 | 7 | 8 | 9 | 10 |
| | Suture Size | | | | | | | | | |
| Physical Property | 2 | 1 | 0 | 2/0 | 3/0 | 4/0 | 5/0 | 6/0 | 7/0 | 8/0 |
| knot pull, kg | 8.07 | 6.02 | 3.99 | 2.70 | 1.43 | 1.08 | 0.62 | 0.33 | 0.15 | .088 |
| straight pull, kg | 9.70 | 6.59 | 4.50 | 3.28 | 1.76 | 1.46 | 0.90 | 0.47 | 0.20 | .128 |
| elongation at break, % | 44.13 | 35.55 | 44.27 | 43.12 | 40.19 | 37.64 | 36.20 | 26.01 | 31.79 | 25.55 |
| tensile strength, kg/mm$^2$ | 36.35 | 34.51 | 37.75 | 38.15 | 39.65 | 48.73 | 54.35 | 59.05 | 89.70 | 70.73 |
| 0–5% energy, kg-mm | 5.32 | 4.51 | 2.46 | 1.89 | 1.10 | 1.03 | 0.62 | 0.40 | 0.13 | .128 |
| 0–10% energy, kg-mm | 23.56 | 18.98 | 10.86 | 7.00 | 4.48 | 4.18 | 2.49 | 1.58 | 0.52 | .463 |
| knot security* | 0/10 | 0/10 | 0/10 | 0/10 | 0/10 | 0/10 | 0/10 | 0/10 | 0/10 | 0/10 |

*Number of knot failures out of 10 samples tested to 100 cycles.

COMPARATIVE EXAMPLES 1–3

These examples compare the average strain energy values of sizes 0, 4/0 and 7/0 of a commercially available polypropylene monofilament suture (Ethicon Inc., Somerville, N.J.) with those of the equivalent sizes of suture herein (Examples 3, 6 and 9) employing the procedure described in Table II. The average strain energy values for the sutures are set forth in Table IV below:

TABLE IV
STRAIN ENERGY VALUES OF POLYPROPYLENE MONOFILAMENT SUTURES

| | Suture Size | Average 0–5% Strain Energy, kg-mm | Average 0–10% Strain Energy, kg-mm |
|---|---|---|---|
| Comparative Example 1 | 0 | 6.29 | 24.31 |
| Comparative Example 2 | 4/0 | 2.22 | 8.72 |
| Comparative Example 3 | 7/0 | 0.28 | 1.12 |
| Example 3 | 0 | 2.46 | 10.86 |
| Example 6 | 4/0 | 1.03 | 4.18 |
| Example 9 | 7/0 | 0.13 | 0.52 |

As these data clearly demonstrate, the sutures of this invention (Example 3, 6 and 9) consistently exhibit significantly reduced levels of strain energy for a variety of suture sizes. Reduced strain energy is a highly desirable characteristic in a surgical suture since the lower the strain energy for a given size suture, the lesser the effort required by the surgeon or assistant personnel to straighten the suture prior to use. Even after prolonged periods of storage, the polypropylene monofilament suture of this invention tends to resist acquiring a set making it all the easier to use the suture directly out of the package with little if any preparative manipulation.

COMPARATIVE EXAMPLE 4

This example compares the knot security of a size 0 commercially available polypropylene monofilament suture (Ethicon Inc., Somerville, N.J.) with that of the equivalent size of suture herein (Example 3) employing the procedure described in Table II. The results of the knot security comparison are set forth in Table V below:

TABLE V
KNOT SECURITY CHARACTERISTICS OF POLYPROPYLENE MONOFILAMENT SUTURES

| | Suture Size | Knot Security |
|---|---|---|
| Comparative Example 4 | 0 | 1/10 |
| Example 3 | 0 | 0/10 |

While none of the knots (out of a total of 10 knots tested to 100 cycles) failed in the case of the suture of this invention (Example 3), 1 out of 10 knots formed with the suture of Comparative Example 4 failed after approximately 10 cycles.

COMPARATIVE EXAMPLE 5

This example compares the 0–5% and 0–10% strain energies of a size 4/0 polypropylene monofilament suture which has been provided by a process identical to that of Example 6 but with a holding period of only 2 hours (Comparative Example 5) which can be essentially regarded as an omission of the equilibration step with the energies of the size 4/0 suture of Example 6 whose manufacture involved a holding period of 4 days to achieve equilibration. The test data are presented in Table VI as follows:

TABLE VI
EFFECT OF HOLDING PERIOD ON PROPERTIES OF POLYPROPYLENE MONOFILAMENT SUTURES

|  | Holding Period | Period Following Annealing When Tested | Average 0–5% Strain Energy, kg-mm | Average 0–10% Strain Energy, kg-mm |
|---|---|---|---|---|
| Comparative Example 5 | 2 hrs | 3 hrs | .82 | 3.3 |
| Comparative Example 5 | 2 hrs | 4 days | .85 | 3.4 |
| Comparative Example 5 | 2 hrs | 3 mos | .91 | 3.8 |
| Example 6 | 4 days | 2 hrs | .75 | 2.9 |
| Example 6 | 4 days | 4 days | .89 | 3.4 |
| Example 6 | 4 days | 3 mos | .83 | 3.4 |

As these data show, both the 0–5% and 0–10% energies of the suture of Comparative Example 5 which had been accorded very little holding time prior to its annealing continuously increased over the entire testing period much in contrast to the suture of Example 6 which, although experiencing an increase in its 0–5% and 0–10% strain energies over a 4 day period, either underwent a significant reduction from the increased level or stabilized at such level. And, consistent with strain energy values data presented in Table IV, supra, the suture of Example 6 tested after 3 months exhibited lower energies than the suture of Comparative Example 5 tested after 3 months.

What is claimed is:

1. In a polypropylene monofilament suture manufacturing process in which an isotactic polypropylene is melt extruded to provide a monofilament and the solidified monofilament is subjected to stretching and annealing to provide the suture, the improvement which comprises equilibrating the stretched monofilament prior to annealing and thereafter annealing the stretched, equilibrated monofilament, equilibration of the stretched monofilament being achieved by storage of the monofilament for a period of at least about 2 days.

2. The process of claim 1 wherein equilibration of the stretched monofilament is achieved by storage of the monofilament for a period of at least about 3 days.

3. The process of claim 1 wherein equilibration of the stretched monofilament is achieved by storage of the monofilament for a period of at least about 4 days.

4. The process of claim 1 wherein the polypropylene possesses a weight average molecular weight of from about 294,000 to about 316,000 and a number average molecular weight of from about 78,400 to about 82,100.

5. The process of claim 4 wherein the polypropylene possesses a melt flow index in g/10 min of from about 2 to about 6.

6. The process of claim 5 wherein the polypropylene possesses a melt flow index in g/10 min of from about 3.5 to about 4.5

7. The process of claim 1 wherein the polypropylene is melt extruded at a temperature of from about 190° to about 230° C. to provide a monofilament and the solidified monofilament is stretched at a temperature of from about 80° to about 180° C. for from about 6 to about 7 times its initial length.

8. The process of claim 7 wherein for suture sizes of 4/0 and smaller, the solidified monofilament is stretched while being heated in an oven chamber maintained at a temperature of from about 90° to about 180° C.

9. The process of claim 7 wherein for suture sizes of 3/0 and larger, the solidified monofilament is stretched while being heated in water maintained at a temperature of from about 80° to abut 98° C.

10. The process of claim 1 wherein for suture sizes of 6/0 and smaller, the stretched monofilament is subjected to a second heat treating operation to effect the on-line shrinkage of the monofilament prior to the monofilament being equilibrated.

11. The process of claim 10 wherein the second heat treating operation is carried out at a temperature of from about 80° to about 130° C.

12. The process of claim 10 wherein the second heat treating operation results in on-line shrinkage of the monofilament for a recovery of from about 97 to about 93 percent of its stretched length.

13. The process of claim 10 wherein the second heat treating operation results in on-line shrinkage of the monofilament for a recovery of from about 96 to about 94 percent of its stretched length.

14. The process of claim 1 wherein for a suture of size 5/0 and greater, annealing in shrinkage of the suture for from about 95 to about 75 percent of its stretched length.

15. The process of claim 1 wherein for a suture of size 5/0 and greater, annealing results in shrinkage of the suture for from about 90 to about 85 percent of its stretched length.

16. The process of claim 1 wherein for a suture of size 2 to 5/0, annealing results in shrinkage of the suture for a recovery of from about 87 to about 83% of its stretched length.

17. The process of claim 1 wherein for a suture of size 2/0 to 5/0, annealing results in shrinkage of the suture for a recovery of from about 92 to about 88% of its stretched length.

18. The process of claim 10 wherein annealing results in essentially no further shrinkage of the monofilament.

19. The process of claim 1 wherein the improved property is at least one of reduced strain energy, increased knot security and reduced out-of-package set.

20. A polypropylene monofilament suture made by the process of claim 2, said suture exhibiting average strain energy parameters in the 0–5% and 0–10% strain energies which, for a given size polypropylene monofilament suture, are at least about 20% less than suture the following average strain energies in the 0–5% and 0–10% strain energy parameters:

| Suture Size | Average 0–5% Strain Energy, parameter kg-mm | Average 0–10% Strain Energy, parameter kg-mm |
|---|---|---|
| 2 | 12.0 | 50 |
| 1 | 10.5 | 42 |

-continued

| Suture Size | Average 0-5% Strain Energy, parameter kg-mm | Average 0-10% Strain Energy, parameter kg-mm |
| --- | --- | --- |
| 0 | 7.5 | 30 |
| 2/0 | 6.0 | 23 |
| 3/0 | 3.5 | 13 |
| 4/0 | 2.5 | 11 |
| 5/0 | 1.5 | 5.5 |

21. The polypropylene monofilament suture of claim 20 having average maximum 0-5% and 0-10% strain energies which, for a given size of suture, are at least about 20% less than the average 0-5% and 0-10% strain energies for that size.

22. The polypropylene monofilament suture of claim 20 having average maximum 0-5% and 0-10% strain energies which, for a given size of suture, are at least about 30% less than the average 0-5% and 0-10% strain energies for that size.

23. The polypropylene monofilament suture of claim 20 having average maximum 0-5% and 0-10% strain energies which, for a given size of suture, are at least about 50% less than the average 0-5% and 0-10% strain energies for that size.

24. The polypropylene suture of claim 20, which for a given polypropylene monofilament suture are about 30% less than the average strain energies in the 0-5% and 0-10% strain energy parameters.

25. The polypropylene suture of claim 20, which for a given size polypropylene monofilament suture are about 50% less than the average strain energies in the 0-5 and 0-10 strain energy parameters.

* * * * *